United States Patent [19]
Simon et al.

[11] Patent Number: 5,607,437
[45] Date of Patent: Mar. 4, 1997

[54] INSTRUMENTS FOR USE IN PERFORMING GEL INJECTION ADJUSTABLE KERATOPLASTY

[75] Inventors: Gabriel Simon, Barcelona, Spain; William G. Lee, Miami Beach; Jean-Marie A. Parel, Miami Shores, both of Fla.

[73] Assignee: University of Miami, Miami, Fla.

[21] Appl. No.: 299,423

[22] Filed: Sep. 1, 1994

Related U.S. Application Data

[63] Continuation-in-part of Ser. No. 836,711, Feb. 19, 1992, Pat. No. 5,372,580, which is a continuation-in-part of Ser. No. 551,807, Jul. 12, 1990, Pat. No. 5,090,955.

[51] Int. Cl.⁶ ................................. A61B 17/00
[52] U.S. Cl. ........................... 606/166; 606/172
[58] Field of Search ...................... 606/107, 166, 606/181, 172; 40/618, 621, 622

[56] References Cited

U.S. PATENT DOCUMENTS

| | | | |
|---|---|---|---|
| 2,550,763 | 5/1951 | Bowder | 40/618 |
| 2,586,009 | 2/1952 | Dickey | 40/618 |
| 2,801,633 | 8/1957 | Ehrlich | 606/181 |
| 3,789,830 | 2/1974 | Malmstrom | 606/181 |
| 4,657,011 | 4/1987 | Gaba | 606/107 |
| 5,071,421 | 12/1991 | Stahl | 606/107 |
| 5,174,279 | 12/1992 | Cobo et al. | 606/107 |
| 5,224,950 | 7/1993 | Prywes | 606/166 |

FOREIGN PATENT DOCUMENTS 735254  9/1977  U.S.S.R.

*Primary Examiner*—Michael H. Thaler
*Attorney, Agent, or Firm*—Jerrold J. Litzinger

[57] ABSTRACT

The present invention provides a surgical technique and instrument kit that allows for subtle modification of the corneal curvature by interlamellar injection of a synthetic gel at the corneal periphery while sparing the optical zone. The gel viscosity, volume and disposition within the surgical annular track as well as the diameter of the track, width, depth, and location are all parameters in the refractive change obtained. Following ultrasonic pachymetry performed centrally and at a selected wound entrance located about 2.5 to 3.5 mm from the apex, a one millimeter or so wide, about 75–85% corneal thickness depth radial incision is performed with a micrometric diamond knife adjusted to about 86% corneal thickness. Inserted through the partial-depth incision, a corkscrew-like dissector or helicoidal spatula forms a 360° annular track centered about the apex. A transparent gel is manually injected through the incision, filling the annular channel. Using a surgical keratometer mounted to an operation microscope, the final corneal power is adjusted by massaging and removing the gel as necessary during the primary procedure or subsequent procedures, as the GIAK technique is reversible.

15 Claims, 12 Drawing Sheets

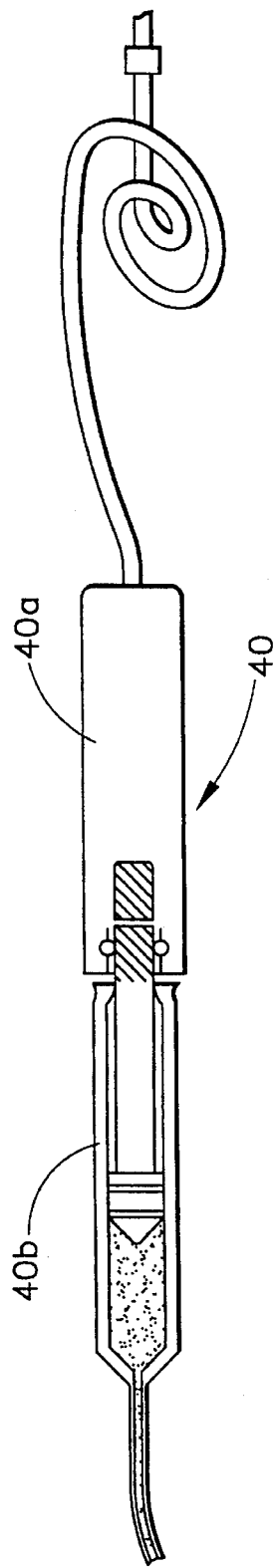
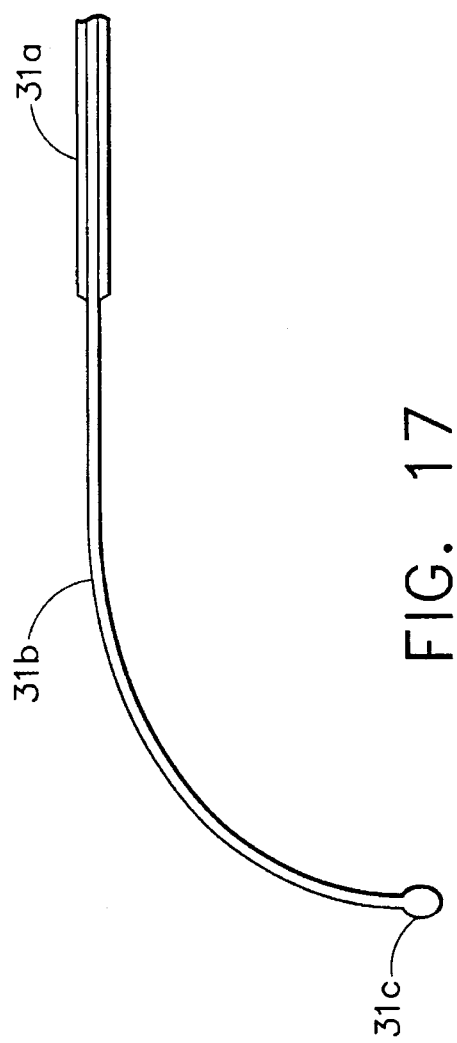
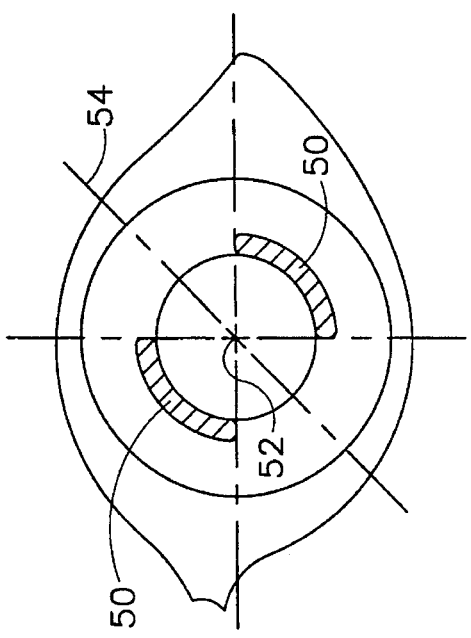
FIG. 16
FIG. 17
FIG. 15

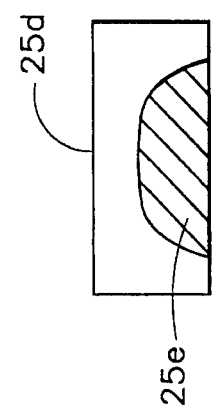
FIG. 22c
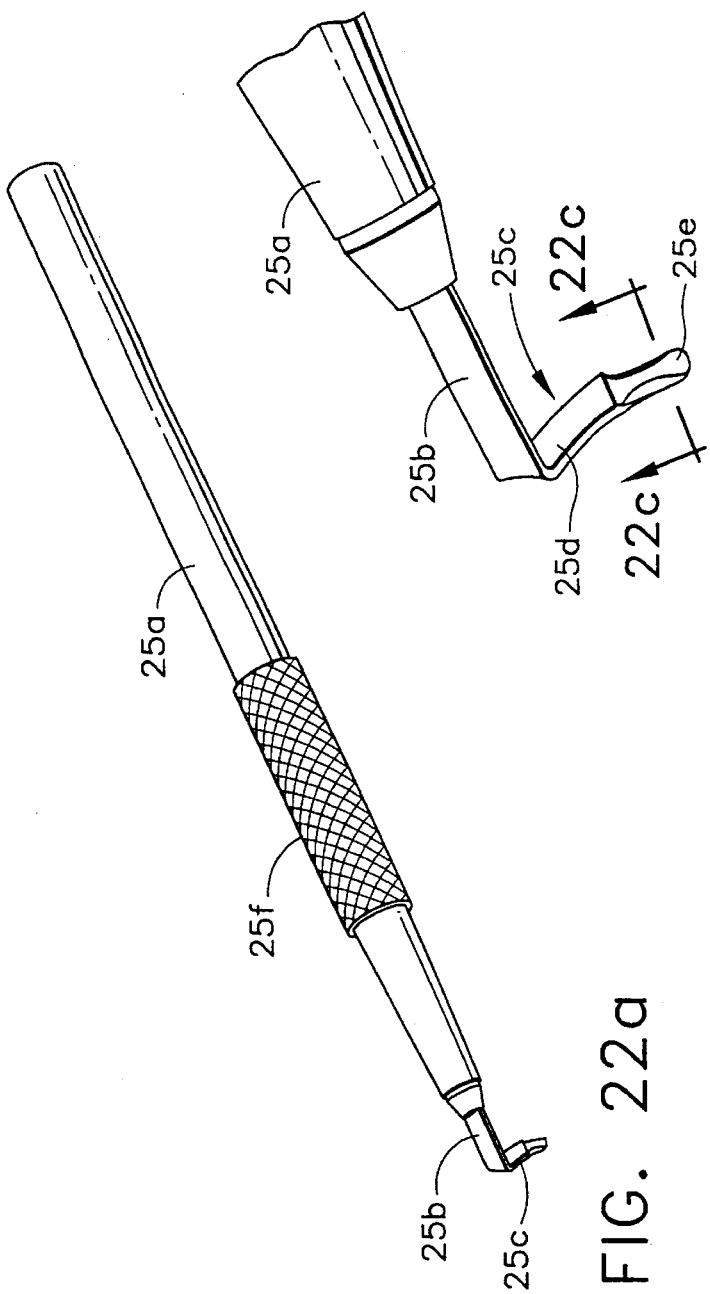
FIG. 22b
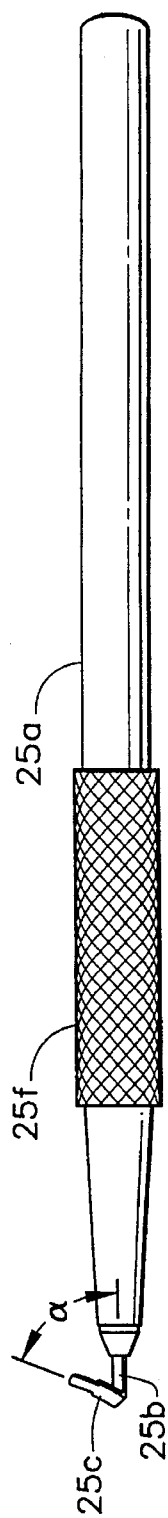
FIG. 22d
FIG. 22a

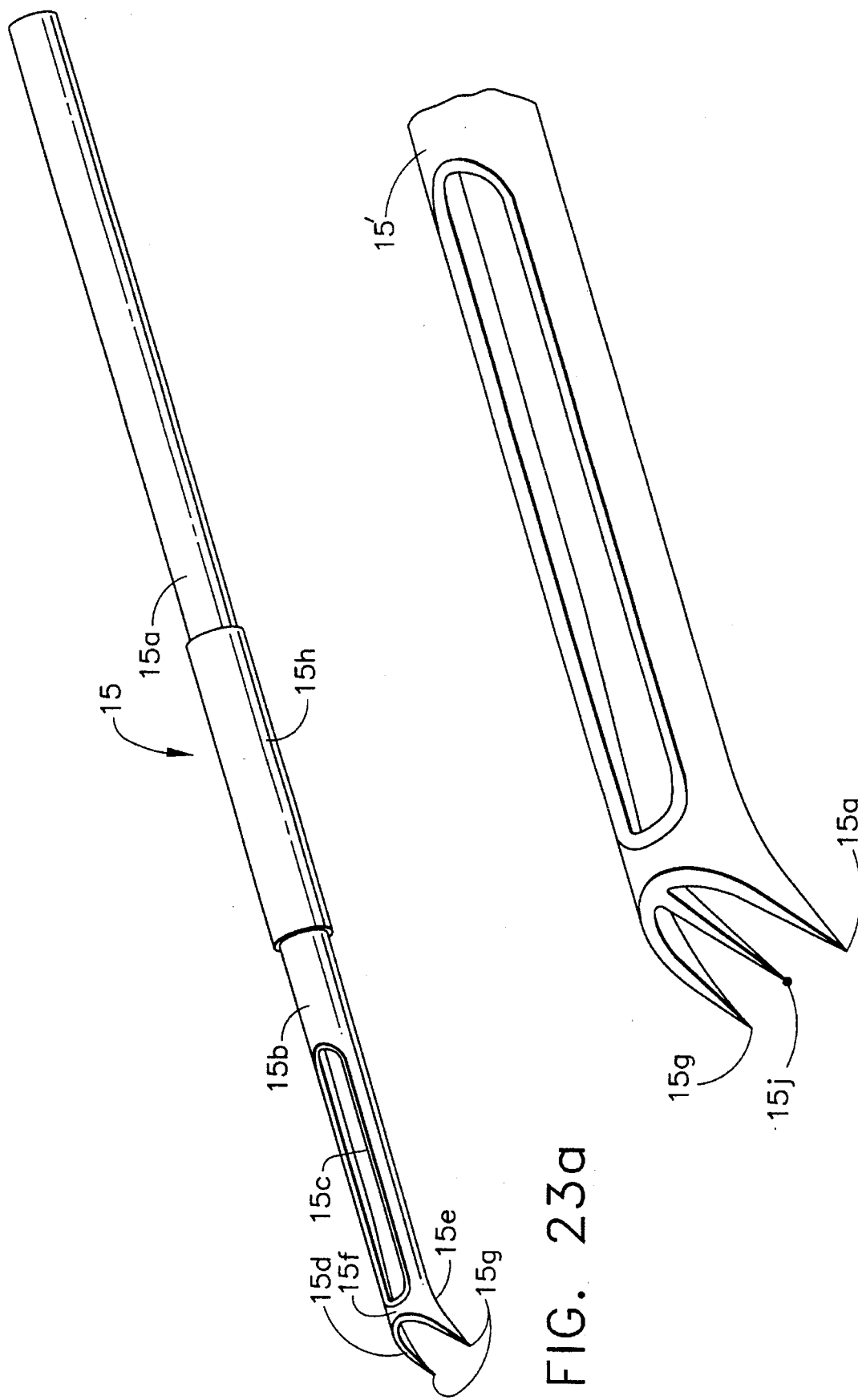

INSTRUMENTS FOR USE IN PERFORMING GEL INJECTION ADJUSTABLE KERATOPLASTY

REFERENCE TO RELATED APPLICATION

This application is a continuation-in-part of U.S. Ser. No. 07/836,711, filed Feb. 19, 1992, now U.S. Pat. No. 5,372,580 which was a continuation-in-part of U.S. Ser. No. 07/551,807, filed Jul. 12, 1990, which is now U.S. Pat. No. 5,090,955.

BACKGROUND OF THE INVENTION

1. Field of Invention

The present invention relates to a technique for intra-operative correction of refractive error to eliminate the need for eyeglasses and contact lenses. More particularly, the invention relates to a technique for surgically correcting myopia and astigmatism by controlled interlamellar annular injection of a polymeric gel at the corneal periphery so as to modify the corneal curvature, while sparing the central optical zone.

2. Description of the Related Art

The ideal surgical procedure in refractive surgery could be defined as one which allows all the advantages of eyeglasses or contact lenses, that is, one which offers effectiveness or a wide range of corrections, allowing correction of ametropias both large and small; accuracy or predictability, allowing for correction of a certain amount of ametropia with precision; alterability or reversibility, so that if ocular refractive changes occur might be possible to adjust the correction again; innocuousness or without complications, that is, the procedure does not lead to adverse situations; visual quality without alterations in the size of the image or of the visual field; technical simplicity, that is, not requiring sophisticated techniques to be put into practice; availability; low cost; and aesthetically acceptable on the part of the patient.

A number of surgical techniques have been proposed which have the object of intra-operative correction of refractive error. Examples are Radial Keratotomy, Keratomileusis, Epikeratoplasty, and Excimer Laser Reprofiling of the Corneal Surface also known as Photo Refractive Keratoplasty (PRK). These methods work with the characteristics of the cornea in order to modify either its curvature or its refractive index. Perhaps the more widespread method and the one which best approaches the objects noted above is radial keratotomy, basically because it can be performed at low cost without the need for additional materials. However this procedure has a number of limitations, including the presence of adverse situations (glare) and a lack of stability, predictability (hypercorrection or hypocorrection) and reversibility. The remaining procedures described and presently in use demand very sophisticated surgical equipment requiring very specialized training and also the use of synthetic or natural materials that reduce the likelihood of the procedure being available in the average clinic. Further, with the present surgical techniques it is not possible to accurately predict the patient's refractive outcome, due in part to corneal hydration and subsequent wound healing processes.

Yet a further prior procedure made use of a rubber annular implant (intrastromal rings) which were surgically inserted to alter corneal curvature. However, that procedure, which was introduced in 1986 by the inventor of the subject procedure, involved stromal delamination of the central optical zone and, in addition, precluded intra-operative or post-operative adjustment of the patient's refractive power.

Therefore, there remains a need for a surgical technique which can achieve intra-operative correction of refractive error to eliminate the need for eyeglasses and contact lenses by modifying the corneal curvature which avoids delamination of the central optical zone and permits intra-operative and post-operative adjustment of the patient's refractive power, and which is also reversible. There further remains a need for such a technique wherein the surgical equipment is relatively inexpensive and only moderate skills are required.

SUMMARY OF THE INVENTION

The present invention describes a technique and set of surgical instruments which allow for the surgical correction of myopia and astigmatism by controlled injection of a polymeric gel or elastomer at the corneal periphery without interfering with the central cornea and endothelium. More particularly, the surgical technique of the invention allows for subtle modification of the corneal curvature by interlamellar injection of a synthetic or natural polymeric gel at the corneal periphery while sparing the optical zone. In accordance with the inventive surgical procedure, a partial depth, radial incision is made outside the optical zone. A corkscrew-like delaminator, for example a helicoidal spatula, is inserted through the incision to form an annular track centered about the corneal apex. A modified needle is then fully or partially inserted in the interlamellar track formed by the delaminator and a transparent gel is manually injected while retracting the needle, thus filling the annular channel, or the gel can be directly injected into the channel. By monitoring the corneal shape with an automatic keratometer, for example, emmetropia can be achieved intra-operatively by controlling the amount of gel injected and by corneal massage. Using a surgical keratometer mounted to an operational microscope, the final corneal power is adjusted by removal of a portion of the gel.

Thus, the use of an injectable substance gives the method, in addition to technical simplicity, the possibility of adjusting the quantity of material to obtain the desired correction. It is also possible to extract or remove this material to reverse the procedure, or augment its volume if necessary.

Other objects, features, and characteristics of the present invention, as well as the methods of operation and functions of the related elements of the structure, and the combination of parts and economies of manufacture, will become more apparent upon consideration of the following description and the appended claims with reference to the accompanying drawings, all of which form a part of this specification, wherein like reference numerals designate corresponding parts in the various figures.

BRIEF DESCRIPTION OF THE DRAWINGS

FIG. 15 is a schematic top plan view of a modified procedure in accordance with the invention;

FIG. 16 is a schematic cross-sectional view of a gel injector suitable for use in accordance with the invention;

FIG. 17 is a plan view of a track width equalizer for use in accordance with the invention;

FIG. 18b is a cross-sectional view of the helicoidal section of the corkscrew delaminator of FIG. 18a;

FIG. 18c is fragmentary enlarged view of one embodiment of the tip of the corkscrew delaminator of FIG. 18a;

FIG. 18d is a fragmentary enlarged view of another embodiment of the tip of the corkscrew delaminator of FIG. 18a;

FIG. 18e is a fragmentary enlarged view of still another embodiment of the tip of the corkscrew delaminator of FIG. 18a;

FIG. 21a is an elevational view of an alternative embodiment of a shoehorn-type device for use in the present invention;

FIG. 21b is a side view of the device shown in FIG. 21a;

FIG. 22a is a perspective view of a channel starting device for use in the present invention;

FIG. 22b is a fragmentary enlarged view of the end of the device shown in FIG. 22a;

FIG. 22c is a cross-sectional view taken along lines 22c—22c of FIG. 22b;

FIG. 22d is an elevational view of the device shown in FIG. 22a;

FIG. 23a is a perspective view of a marking instrument for use in the present invention;

FIG. 23b is a fragmentary view of an alternative embodiment of the instrument shown in FIG. 22a.

DETAILED DESCRIPTION OF THE PRESENTLY PREFERRED EXEMPLARY EMBODIMENT

The exact physical properties of the cornea and scleral limbal tissues have not been determined. However, if the cornea resists stretching, it can easily be delaminated. The large differential in modulus of elasticity between the two orthogonal corneal planes is responsible for the effects observed with the procedure of the invention.

The corneal lamellae are laid parallel to Bowman and Descemet layers and have a radial elastic modulus of approximately $5 \times 10^6$ N/m$^2$ and a transverse elastic modulus of $3 \times 10^4$ N/m$^2$. These lamellae are weakly bounded and can be easily separated.

The scleral-limbal region forms an annulus (the corneal limbus) much more rigid than the cornea and act as a reference frame with respect to corneal deformation. With the procedure of the invention, the limbus geometry and physical characteristics remain stable (unchanged). Therefore, the procedure of the invention causes a redistribution of the nominal corneal stresses produced by the positive intraocular pressure. This redistribution causes a change in the corneal shape with a flattening of the central corneal radius of curvature and a steepening of the site of gel injection. However, the inner and outer corneal surface areas are kept constant. Therefore, little change occurs in stress applied along the individual lamella. As the laminar network is kept intact except for the small incision site, a very minimal wound healing effect is expected. Thus, the keratometric changes produced by the procedure of the invention are expected to be stable in long-term follow up.

Figure 1:
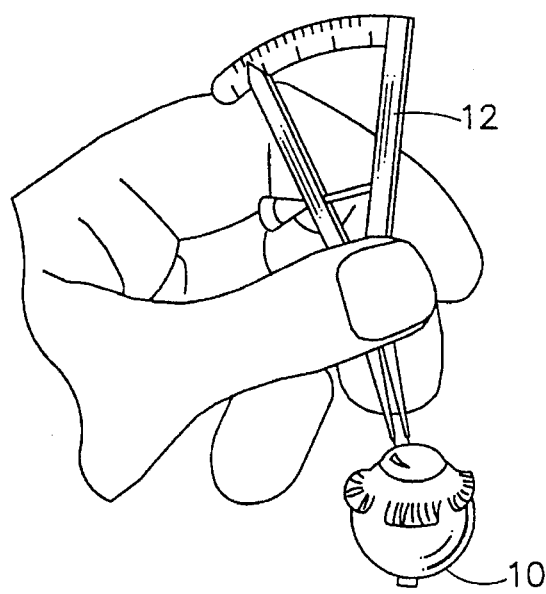
FIG. 1 is a schematic perspective view showing the use of a caliper to locate and mark the central cornea and incision site in accordance with the invention.
Figure 2:
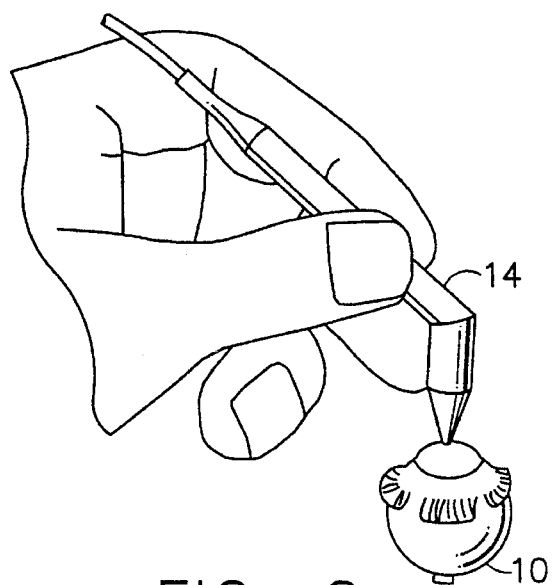
FIG. 2 is a schematic perspective view of an ultrasonic pachymeter for measuring corneal thickness in accordance with the procedure of the invention.

The procedure in accordance with the invention is as follows:

First, the central cornea and the incision site are defined and marked on the eyeball 10 with the help of a standard caliper 12 as shown in FIG. 1. Specifically, the surface of the eyeball is dried with blotting paper and marked with a compass, for example a Castroviejo Caliper #E 2404 available from Storz, Inc. having blunt needles or points which have been previously soaked with ink from an epidermic labeler, such as #150 available from Devon, Inc. The ink soaked needles are placed on the eyeball to mark the corneal center and the incision site between about 2.5 and 3.5 mm from the apex, a distance corresponding substantially to the internal radius of the corkscrew delaminator used to form the intra-laminar canal in accordance with the invention. Additional marks may be made at that predetermined distance from the corneal center to mark a guide for the dissector to follow during the surgical maneuver. Once the central cornea and incision site have been selected and marked, the corneal thickness is determined with a conventional ultrasonic probe and pachymeter 14 at the corneal center and at the incision site as shown schematically in FIG. 2.

An instrument for facilitating the marking of the cornea for the incision site is shown in FIG. 23a. Marking instrument 15 consists of a handle section 15a and a guide section 15b. Guide section 15b has an opening 15c and a pair of parallel arms 15d and 15e which are connected by a rounded section 15f. Parallel arms 15d and 15e terminate in a pair of points 15g. Instrument 15 is used by aligning the apex of rounded section 15f with the corneal center, such that points 15g of parallel ends 15d and 15e will indicate the inner diameter of the channel formed by the delaminator. In the present embodiment, the distance between points 15g is preferably 5 mm. Finally, a raised section 15h on handle section 15a offers the surgeon a comfortable and secure grip when using instrument 15.

A second embodiment of instrument 15 is shown in FIG. 23b as 15'. Instrument 15' contains a central prong 15j located between points 15g. Prong 15j acts a centering device, which when positioned at the corneal center, locates points 15g at the proper incision sites.

Figure 3:
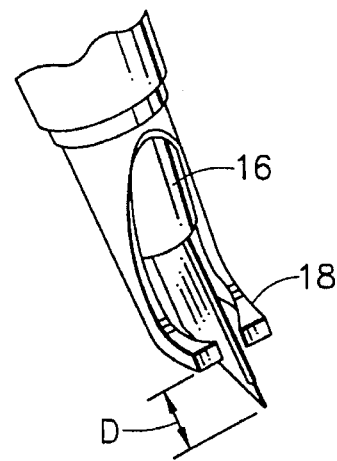
FIG. 3 is a perspective view of a diamond knife equipped with a micrometer.
Figure 4:
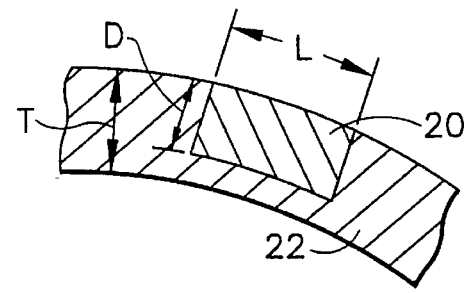
FIG. 4 is a schematic cross-sectional view of an incision formed in accordance with the invention.
Figure 5:
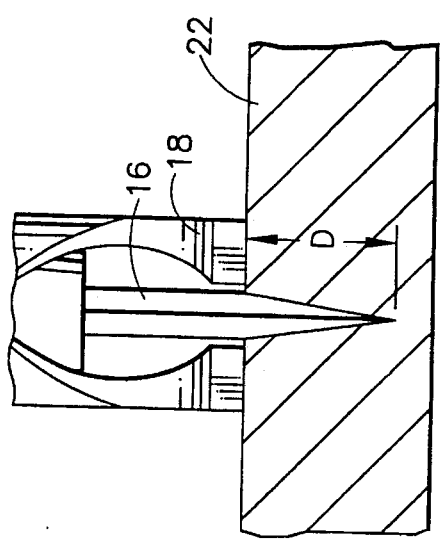
FIG. 5 is a schematic elevational view showing the incision of the cornea in accordance with the invention.

A partial depth incision 20 is then performed at the incision site with a diamond knife 16 which is equipped with a micrometer (not shown) having a footplate 18 (FIG. 3). The blade length is adjusted to about 86% of the corneal thickness, as measured by the pachymeter. The knife is then used to form a radial incision to a depth D of between 75% and about 85% and most preferably between about 75% and about 80% of the corneal thickness T. To obtain a flat-bottomed incision with vertical walls, the diamond blade can be reversed and moved radially with respect to the center of the cornea (FIG. 4). The foregoing two step procedure with the diamond blade can be avoided by the use of a flat-edged blade. The insertion of the diamond knife 16 to the predetermined 80%±5% depth of the cornea 22 is illustrated in particular in FIG. 5. The incision is performed to a length L of about 1.0 mm or less and most preferably about 0.4 mm which is preferably between 0 to 0.5 mm less than the width of the delaminator to be used. The incision is preferably made as small as possible so as to minimize wound healing time following the procedure.

Figure 6:
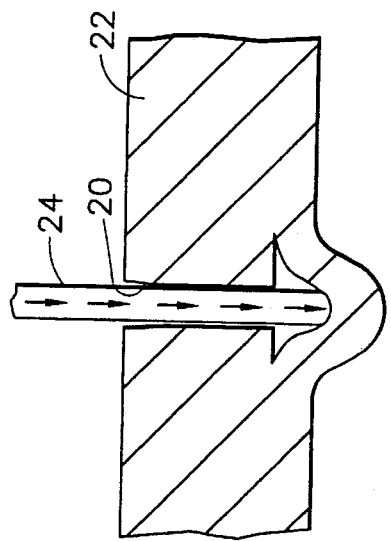
FIG. 6 is a schematic elevational view showing the insertion of a blunt spatula in accordance with the invention for separating the lamella.

Once the incision has been formed, a spatula 24 such as, for example, a Castroviejo cyclodialisis spatula #E 0292 available from Storz, Inc. having dimensions identical to that of the helical spatula, for example about 1 mm or less in width and 200 micrometers in thickness and having an end which is slightly modified by being polished to a point, is inserted through the incision to separate the lamella in the plane of the base of the incision (FIG. 6). The particular width of the spatula used of course depends upon the length of the incision. Alternatively, once the incision has been made to the desired depth in the cornea, an instrument is inserted into the incision to locate the proper plane along which to separate the lamella and form the intralamellar canal in accordance with the invention. A channel starting instrument 25 (FIGS. 22a–d) consists of a handle 25a, a central section 25b, and end section 25c. Central section 25b is preferably coaxial with the central axis of handle section 25a, and is formed from a flat wire. As can be seen in FIG. 22d, end section 25c, which is shown as curved but may be linear, is attached to central section 25b at an acute angle α to the central axis through sections 25a and 25b, which angle is preferably between 40° and 45°. End section 25c consists of a curved or arcuate portion 25d and a smaller portion 25e which is also curved. Preferably, section 25c is constructed having the same radius of curvature of the helical spatula to be used for the procedure. Portion 25d is formed out of a flat wire, while portion 25e consists of a semicircular section of curved wire, as can be most clearly seen in FIG. 22c.

Instrument 25 is used by inserting end section 25c into incision 20 until section 25c contacts the bottom of the incision. Handle section 25a is then rotated in a manner such that the lamella is separated along an arcuate path by curved portion 25e of end section 25c. Handle section 25a contains a knurled portion 25f to assist the user in gripping the instrument.

Figure 7:
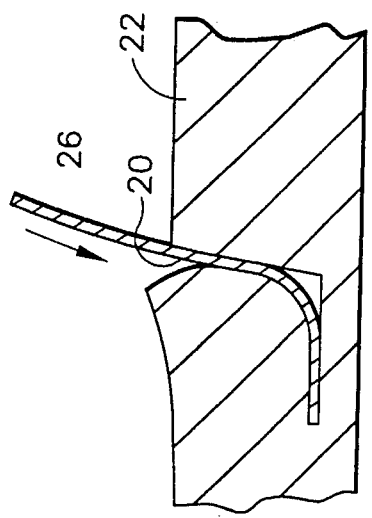
FIG. 7 is a schematic elevational view of the insertion of a shoehorn-like device for facilitating insertion of a corkscrew delaminator in accordance with the invention.

Following the initial separation of lamella with the blunt spatula 24 and starting the channel with instrument 25, a shoehorn-type device 26 is inserted through the incision and laterally between the lamella as shown in FIG. 7. The shoehorn-type device 26 can be made of plastic or stainless steel or any material which is more rigid than the radial elastic modulus of the cornea, which measures approximately $5\times10^6$ N/m$^2$. The thickness of device 26 may approach 300 microns, with the preferred range being between approximately 50 to approximately 100 microns.

Figures 21A, 21B:
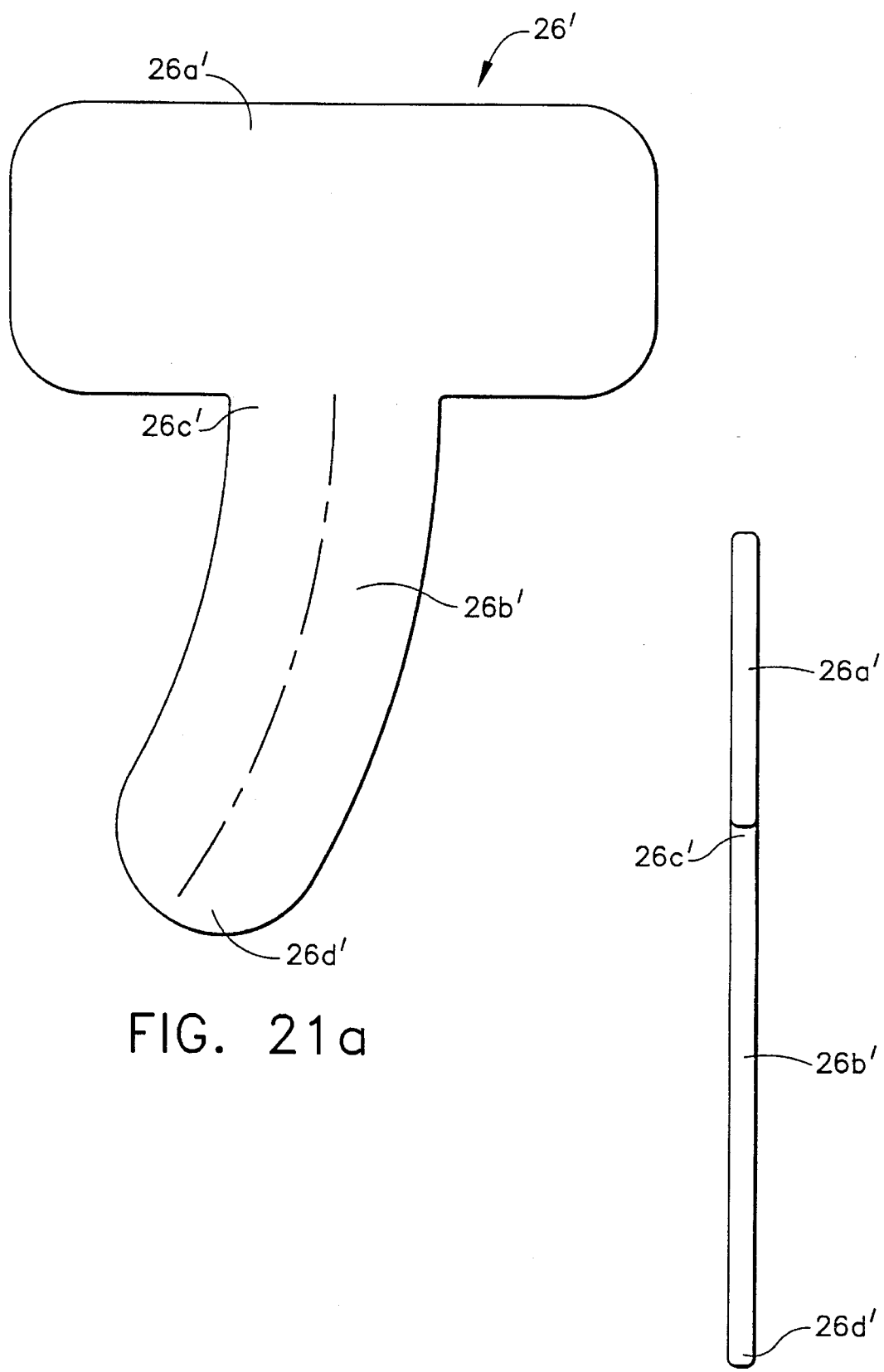

An alternative embodiment of shoehorn-type device 26 is more clearly shown in FIGS. 21a and 21b. Referring now to FIGS. 21a and 21b, device 26' is a planar member having an upper horizontal section 26a' and a downwardly depending extension 26b'. The upper end 26c' of extension 26b', which is narrower than upper section 26a', depends from the central region of section 26a' at an approximate angle of 90°, and extension 26b' may be either slightly curved or straight as it continues away from upper section 26a' until it reaches its lower end 26d', which end is rounded for ease of insertion into the incision. The length of extension 26b' may range between 1 and 6 mm, while its width should be less than or equal to the width of the delaminator.

Ideally, the radius of curvature of extension 26b' should match the radius of curvature of the helical delaminator.

Extension 26b' of device 26' is inserted into the incision until upper section 26a' contacts the upper surface of cornea 22. The curvature of extension 26b' of device 26' facilitates the insertion of spatula 28 to the proper plane for delamination which has been selected and started by instrument 25 and guides spatula 28 as it begins to form annular chamber 30. The design of shoehorn-type device 26' also provides for easier insertion and extraction of device 26' from the incision site.

Figure 8:
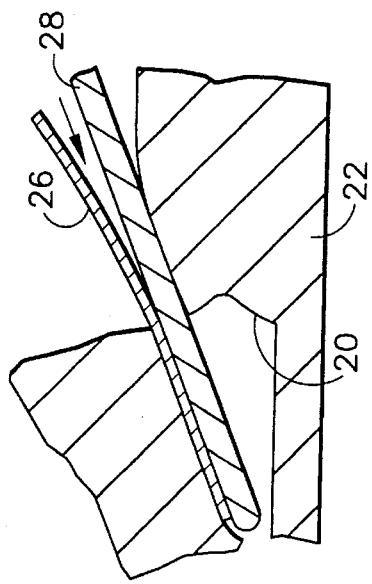
FIG. 8 is a schematic elevational view of the insertion of a corkscrew delaminator.

The shoehorn-type instrument is utilized for facilitating insertion of a corkscrew delaminator or helicoidal spatula 28, for example a custom made Archimedes-screw dissector which is inserted behind or under shoehorn device 26, as shown in FIG. 8. The flat corkscrew delaminator is used to carve a circular canal between the two corneal lamellae in which a gel such as a silicon gel is subsequently injected. The illustrated corkscrew delaminator consists of a flat wire between 0.25 and 4.5 mm, preferably about 1 mm in width as in the preferred embodiment, again depending upon incision length and 0.1 mm in thickness, and is curved to about 380°, that is superimposed by 20°. The spatula's edges are blunt or rounded as is its end. The inner diameter of spatula 28 may fall within the range of 2.0 to 10.5 mm, with the preferred embodiment measuring approximately 5 mm.

Figure 9:
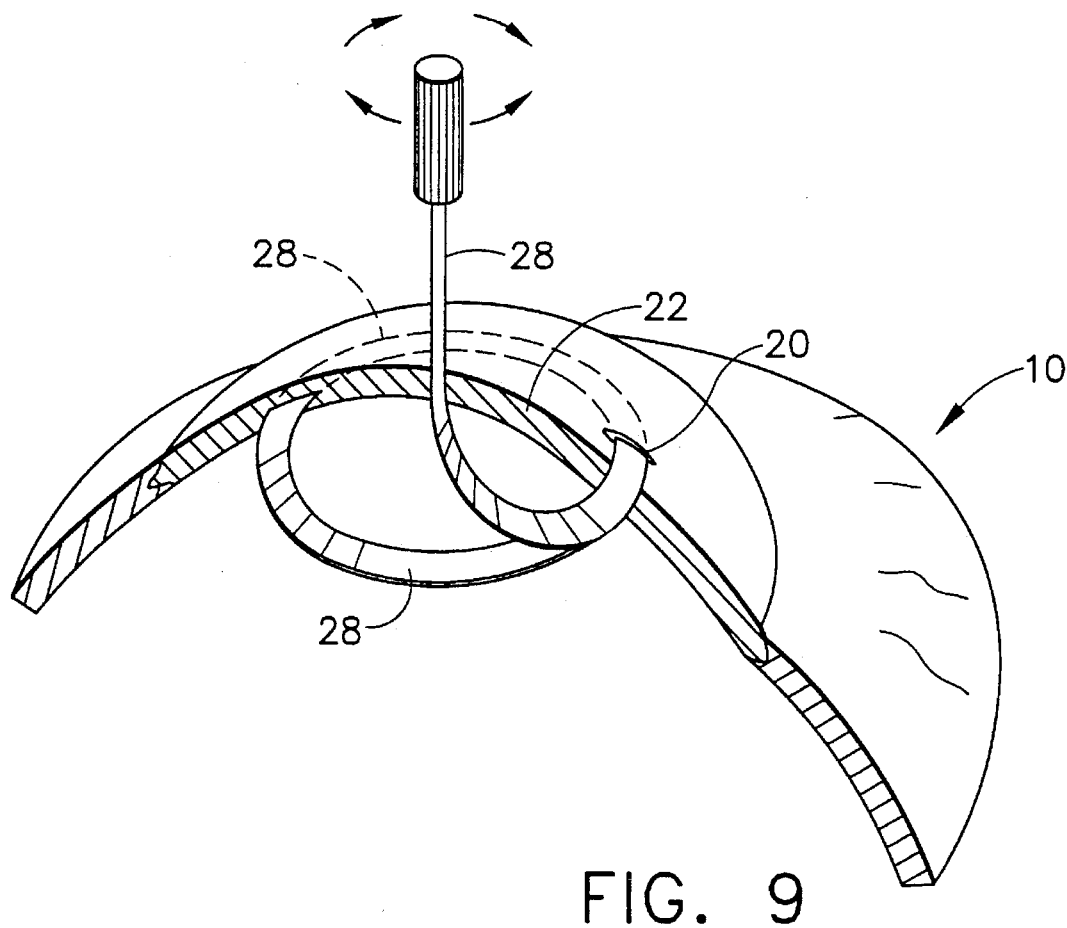
FIG. 9 is a perspective view, partly in cross-section and partly broken away for clarity, illustrating the formation of an annular track with a corkscrew delaminator in accordance with the invention.
Figure 10:
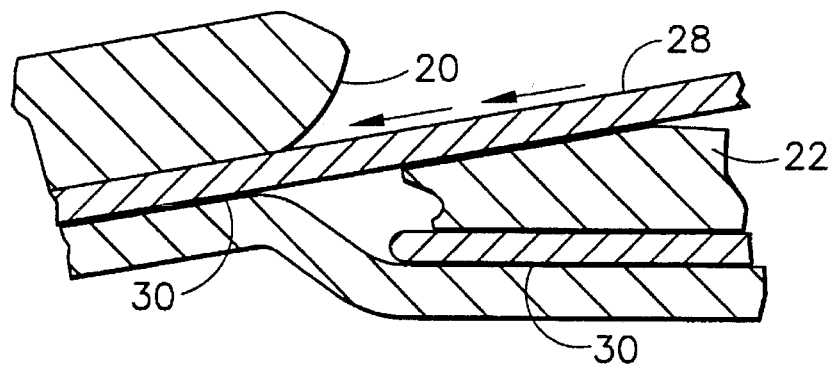
FIG. 10 is a schematic elevational view of the incision site following complete insertion of the corkscrew delaminator.

As shown in FIG. 9, with the corkscrew delaminator, an annular track is made through the cornea at the preselected plane. A full 360° twisting motion of the helicoidal spatula 28 delaminates the cornea completely at the radial location of the incision, circumferentially of the central corneal zone. However, the central and paralimbal zones of the cornea are not delaminated as the helicoidal spatula 28 limits the delamination to an annular path at the radial locus of the incision. As shown in FIG. 10, the annular delamination results in the formation of an annular chamber or canal 30 opening on either side of the initial incision 20. Following the annular delamination, the helicoidal spatula 28 is removed by rotating the same with a reverse 360° twisting motion. When spatula 28 is removed, it may be necessary to ensure that the canal 30 openings on either side of the initial incision 20 are uniform to allow for the proper flow of gel through canal 30. A track width equalizer 31 (FIG. 17) is used for this purpose. Equalizer 31 contains a handle portion 31*a*, a curved portion 31*b*, and a rounded end portion 31*c*. End portion 31*c*, which typically measures 0.5 mm in diameter, is inserted through incision 20 into each canal 30 opening, thus insuring that the injected gel will pass through canal 30. Equalizer 31 is also used to remove the gel if necessary.

A small corkscrew-like cannula 32, in the range of 19 to 30 gauge in size, preferably 30 gauge in the present embodiment, is then inserted into the annular channel 30. A syringe, for example filled with a biocompatible gel, is attached to the corkscrew cannula 32 following insertion or prior to insertion into the annular channel 30. Examples of suitable biopolymeric materials for the gel are known biocompatible hydrogels (e.g. acrylic hydrogels, polyethylene oxides), silicone-based cross-linked elastomers, and other biopolymers (e.g. cross-linked hyaluronic acid). One gel which has been found to be suitable for use in the present invention is a crosslinked polyethylene oxide (PEO) gel which is prepared by dissolving a sample of PEO in a Balanced Salt Solution (BSS), placing the solution in a sealed canister, removing any free oxygen from the interior of the canister, replacing the oxygen with an inert gas such as argon, irradiating the canister to crosslink and sterilize the PEO, and loading the sterilized PEO into a sterile syringe. This method is more completely described in co-pending application Ser. No. 08/299,583, which was filed on the same date herewith and is assigned commonly herewith. The disclosure of the pending application is incorporated herein by reference. This gel has a modulus of elasticity of approximately $1.7 \times 10^3$ n/m$^2$ and an index of refraction of 1.334. Once the corkscrew cannula is inserted, injection is started (FIG. 11).

It is also possible to inject gel 34 directly into canal 30 by using an automatic injector 40 (FIG. 16). Injector 40 consists of a powered injector unit 40*a* and a gel cartridge unit 40*b*. Unit 40*a* can be controlled by a manual switch on the unit, or by a foot pedal switch. Cartridge 40*b* is a disposable sealed unit to prevent contamination, and fits onto unit 40*a* for easy, sterile operation. Injector 40 provides a consistent force to inject gel 34 into canal 30.

Figure 24:
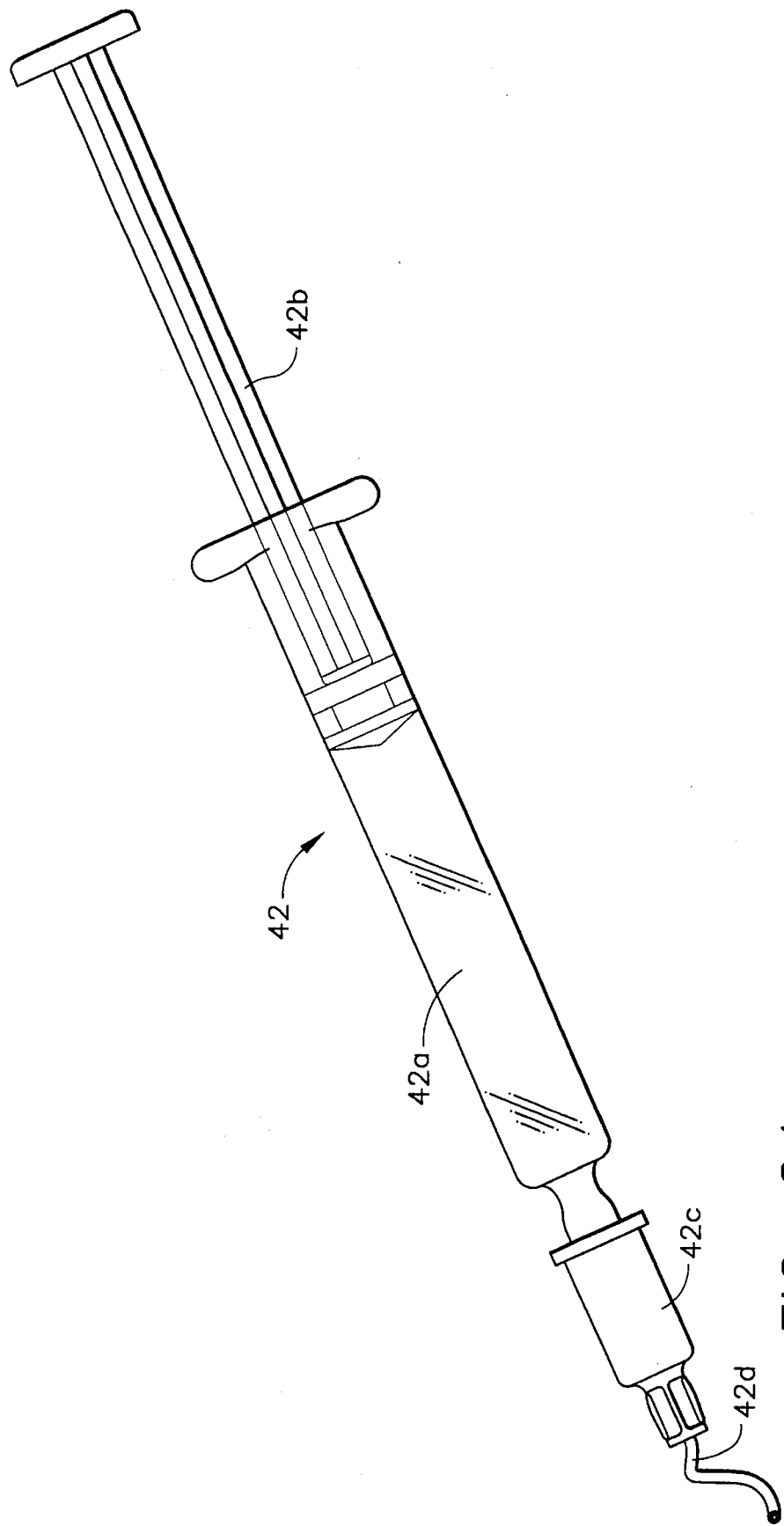
FIG. 24 is a perspective view of a syringe for use in the present invention.

Another alternative for injecting gel 34 into canal 30 is shown in FIG. 24. A syringe 42 having a gel storing compartment 42*a*, a plunger 42*b* captively held with compartment 42*a*, and a cannula 42*c* coupled to the end of compartment 42*a* may be used to inject gel 34. Cannula 42*c* has a curved end 42*d* which is helicoidal or spiral shaped such that it can be easily inserted through incision 20 and into canal 30, thus insuring that gel 34 will completely fill canal 30 as syringe 42 is operated. The curvature of end 42*d* of cannula 42*c* is preferably matched to the curvature of helicoidal spatula 28.

Figure 11:
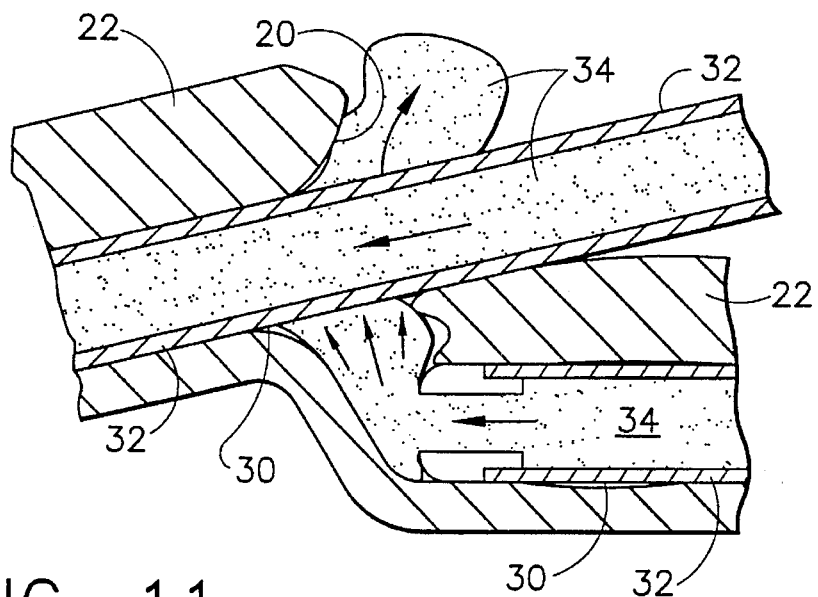
FIG. 11 is a schematic cross-sectional view showing the injection of gel with the needle in accordance with the invention.
Figure 12:
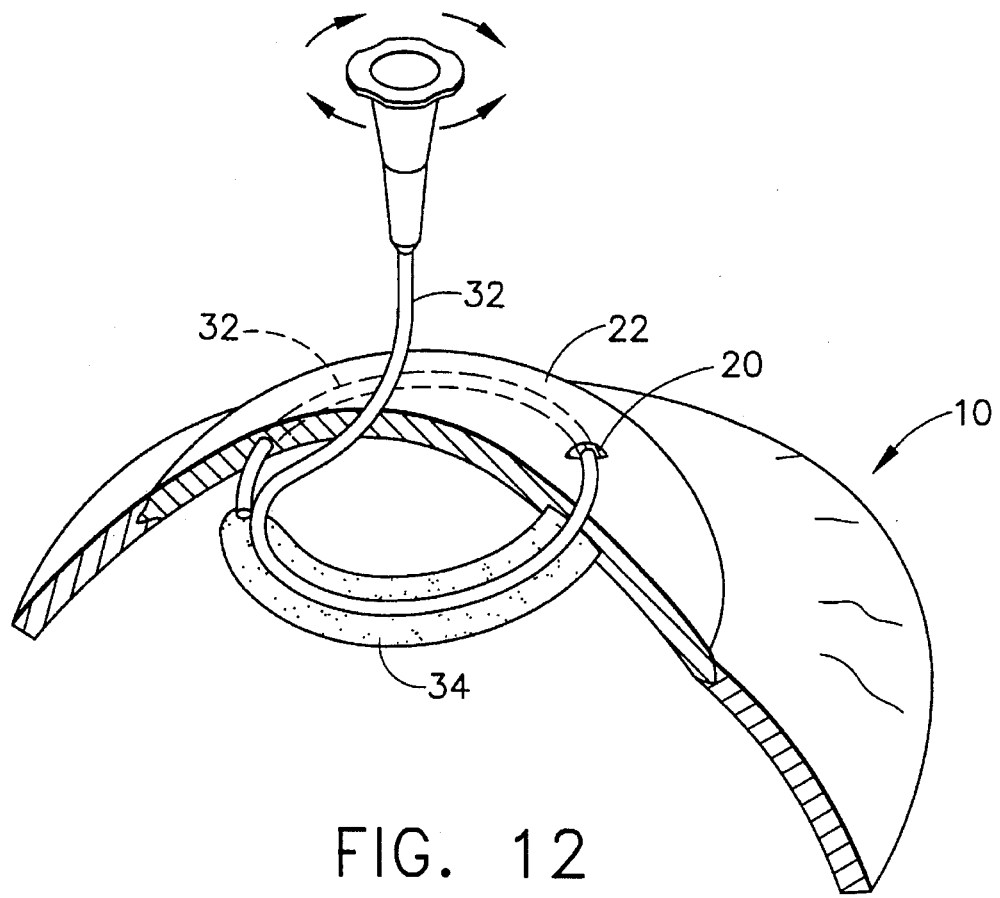
FIG. 12 is a perspective view, partly in cross-section and partly broken away for clarity, showing the retraction of the needle while the gel is injected.
Figure 13A:
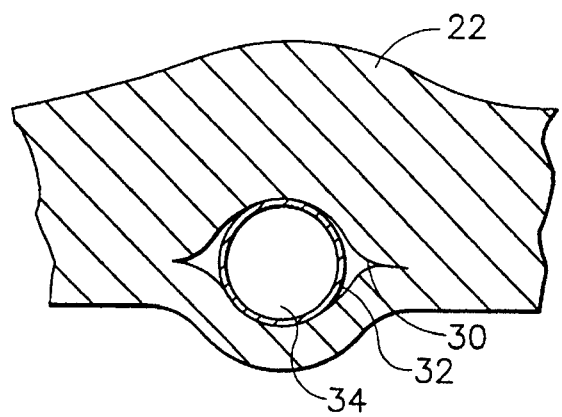
FIG. 13a is a schematic cross-sectional view of the cornea with the needle within the annular track.
Figure 13B:
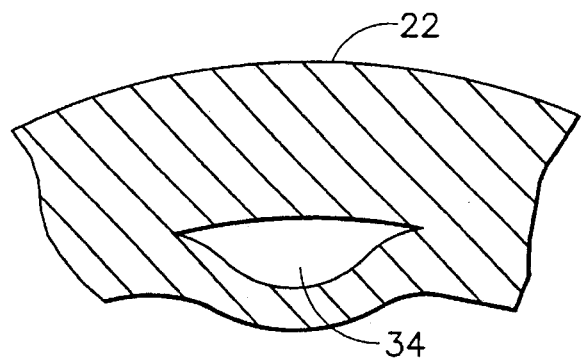
FIG. 13b illustrates the track with gel so as to bulge the corneal posterior lamellae and flatten the central corneal optical zone.

A small amount of gel escapes from the corneal incision due to over pressurization (FIG. 11). Furthermore, subsequent to needle removal, an external massage is performed in order to evenly distribute the gel inside the canal. The remaining gel that appears at the incision is grabbed with forceps and cut, for example with scissors. Once the 30 gauge needle has been removed, gel fills the track creating a bulging of the corneal posterior lamellae and a flattening of the central corneal optical zone. FIG. 13*a* is a corneal cross-section illustrating the displacement of the corneal lamella when the needle 32 is disposed with an annular track 30. Once the needle has been retracted and gel fills the annular canal 30, a bulging of the cornea posterior lamella and a flattening of the central corneal optical zone occurs (FIG. 13*b*). Up to 13 diopters of flattening have been obtained in cadaver eyes with the technique of the invention. By removing a portion of the gel from the channel, the amount of corneal flattening can be reduced until emmetropization has been achieved. Intraoperative keratometry is suggested for determination of optimal corneal radius of curvature although other techniques could be employed. The amount of correction obtainable is a function of the inner diameter and wire width of the delaminator, in addition to the amount of gel used.

Figure 14:
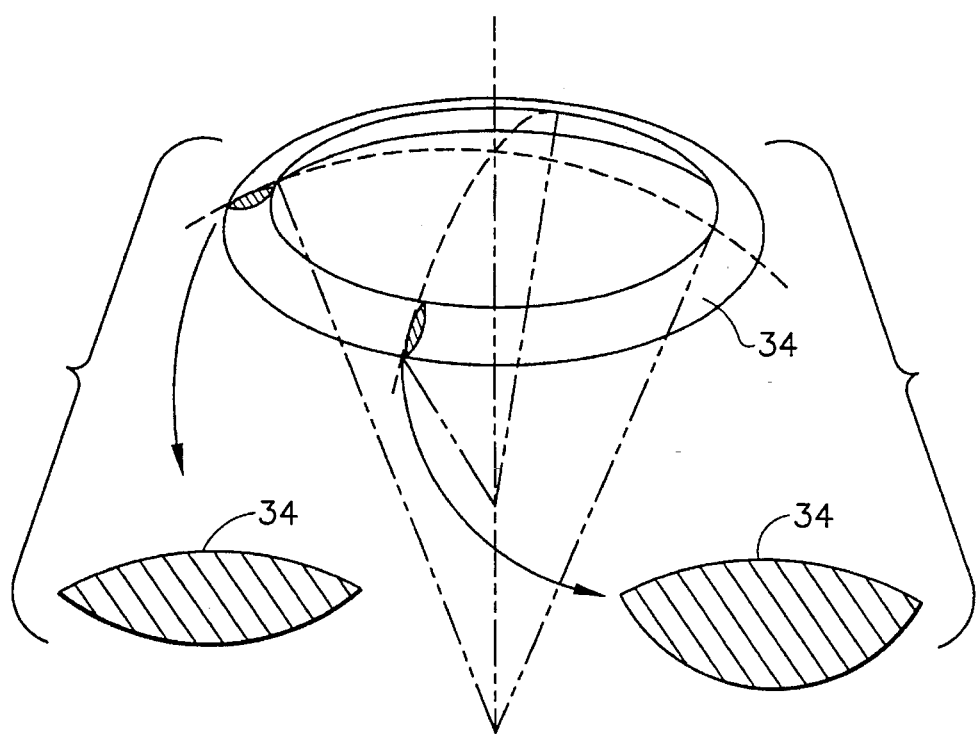
FIG. 14 is a schematic perspective view illustrating localized corneal shear variations generated at the limbus which produces astigmatism and their effect on the gel injected in accordance with the invention.

Referring to FIG. 14, astigmatism is thought to be produced by localized corneal shear variations generated at the limbus. With the process of the invention, a reduction of existing astigmatism was observed experimentally. This phenomenon can be explained by a localized variation in gel distribution along the annular channel as shown. Indeed, because the pressure of the gel is constant, it equilibriates the radial stresses along the corneal meridian.

Astigmatism may also be corrected in accordance with the present invention by using a modified procedure as illustrated schematically in FIG. 15. In accordance with this modified procedure, a pair of arcuate channels 50 of approximately 90° in arc length and centered about the corneal center 52 are made by a stromal delaminator (not shown) which is a shorter version of the helicoidal delaminator discussed in detail above. A gel, as discussed above, is then injected into each of the arcuate channels 50 under keratometric control. The magnitude of the astigmatic optical correction in diopters is a function of the amount of gel injected into each of the arcuate channels 50, the size, that is diameter, width and angle of the arcuate channels, and the position of the two arcuate channels with respect to the patient's corneal astigmatic (flattest) axis 54.

As noted above, minimizing the length of the incision, in accordance with the invention, reduces wound healing time. To further reduce wound healing time, following gel injection and the removal of any excess gel, the corneal incision can be instantly closed-shut by applying a very small amount of collagen gel to the upper lips of the wound and cross linking it with ultraviolet radiation. Such sealing of the incision eliminates post operative patching of the eye and thus allows the patient to walk away from surgery without impediment. Ultraviolet cross linkable collagen gels are fabricated by several manufacturers and a suitable ultraviolet cross linkable collagen gel among those available could be readily ascertained.

Another advantage of the present invention over current surgical techniques is reversibility. Should it become necessary to readjust the curvature of the cornea at some later time, such as a year later, a linear incision is made above the channel to a depth which intersects the channel. The gel can then be removed by massaging the cornea or additional gel may be added as previously described until the desired corneal shape is obtained and then the incision is closed using the above described technique.

FIGS. 18*a*–18*e* show alternative embodiments of a helicoidal delaminator or spatula for use in the present invention. Spatula 44 consists of a helicoidal section 44*a*, a planar support section 44*b*, and a handle section 44*c* which is fixed to support section 44*b* by welding or a similar attachment means. Handle 44*c* allows helicoidal spatula 44 to be more easily manipulated during surgery. The design of handle 44c, consisting of an annular cylindrical ring, is important, as it allows the surgeon an unobstructed view of the corneal surface as he is using the device. Handle 44c of spatula 44 is provided with a pair of indicating marks 60 and 62 on its upper surface. Marks 60 and 62 may be used to indicate relative position of section 44a of spatula 44 when it is within channel 30 that has been formed in cornea 22, as section 44a is no longer visible. Mark 60 is used to indicate the position of the end of the nose portion of helicoidal section 44a so that the surgeon can determine when he has completed the formation of channel 30. Mark 62 indicates where the overlapped portion of helicoidal section 44a begins. Marks 60 and 62 facilitate the use of spatula 44 during the procedure by eliminating uncertainty with respect to its position.

Figure 18A:
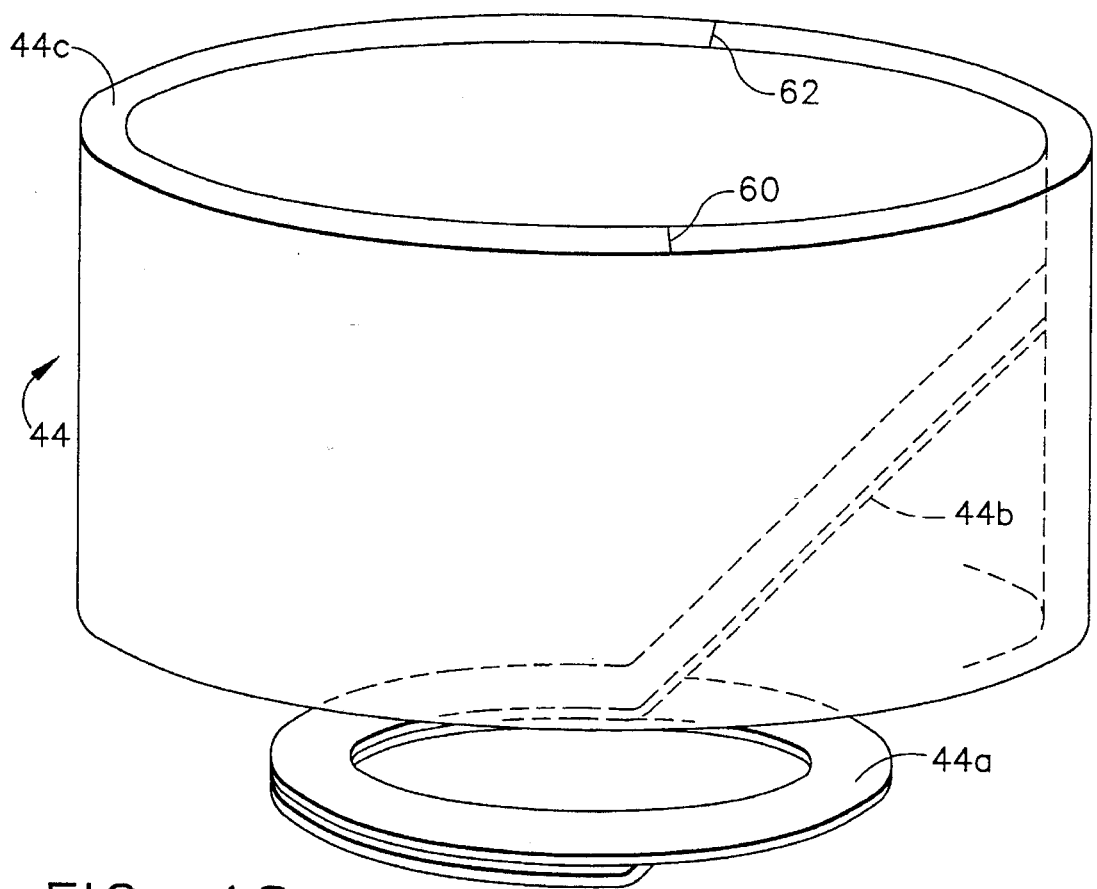
FIG. 18a is a perspective view, partly in phantom, of a different embodiment of the corkscrew delaminator in accordance with the invention.
Figure 18B:

FIG. 18b shows the cross-section of the helicoidal section 44a of spatula 44. It can be seen that section 44a imitates the radius of curvature of the cornea, which is approximately 7.8 millimeters, such that channel 30 closely parallels the surface curvature of the cornea.

Figure 18C:
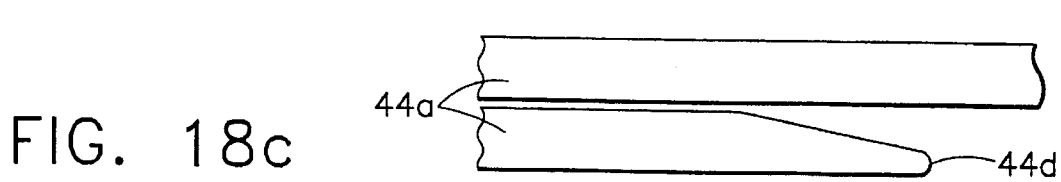
Figure 19:
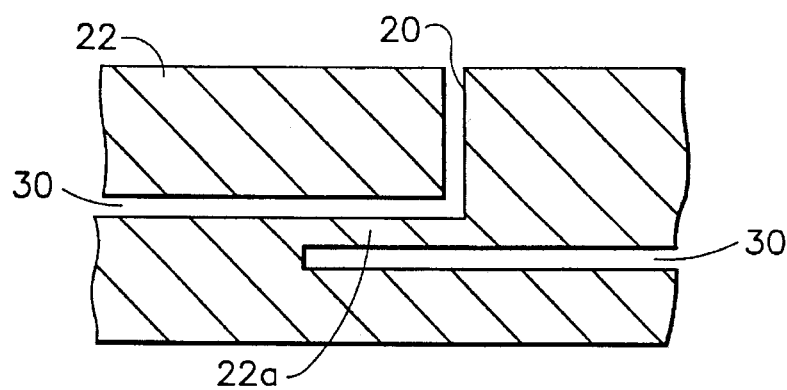
FIG. 19 is a schematic cross-sectional view of the annular track formed in the cornea with the delaminator shown in FIGS. 18a and 18c.

In the embodiment shown in FIG. 18c, spatula 44 contains a nose portion 44d which is tapered along the top edge toward its end. When spatula 44 is used in the corneal surgical procedure described in the present invention, nose portion 44d creates a lameliar flap within the track formed by spatula 44 within the cornea. As can be seen in FIG. 19, lameliar flap 22a within cornea 22 aids in sealing channel 30 from incision 20, thus preventing gel from freely escaping from incision 20. Thus, this modification to spatula 44 eliminates the need for adhesives or the like to bond the incision in the cornea. Nose portion 44d tends to keep channel 30 in the lower portion of the cornea.

Figure 18D:
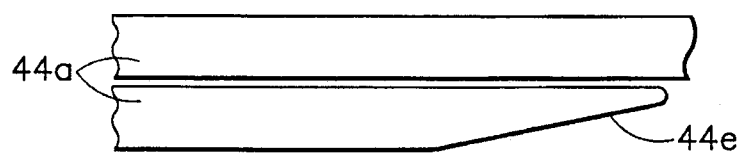
Figure 20:
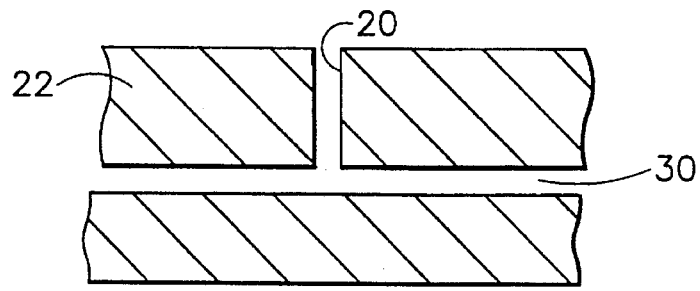
FIG. 20 is a schematic cross-sectional view of the annular track formed in the cornea with the delaminator shown in FIGS. 18a, 18d and 18e.

FIG. 18d shows an alternative embodiment of the end of spatula 44. Nose portion 44e is tapered along the bottom edge of section 44a toward its end. When spatula 44 is used in the corneal surgical procedure described in the present invention, nose portion 44e creates a channel as shown in FIG. 20. This channel 30 intersects incision 20 directly. Nose portion 44e tends to keep channel 30 in the upper portion of cornea 20.

Figure 18E:
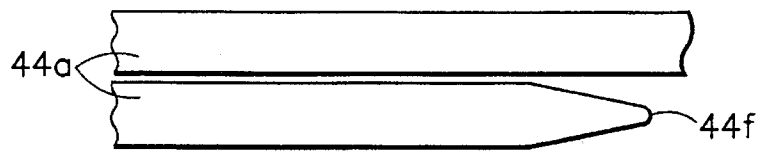

FIG. 18e shows another alternative design for the end of spatula 44. Nose portion 44f is v-shaped at the end of spatula 44, and also creates a channel as shown in FIG. 20. Nose portion 44f tends to keep channel 30 in the middle portion of cornea 20.

While the invention has been described in connection with what is presently considered to be the most practical and preferred embodiment, it is to be understood that the invention is not to be limited to the disclosed embodiment, but on the contrary is intended to cover various modifications and equivalent arrangements included within the spirit and scope of the appended claims.

Indeed, while the presently preferred incision location and depth which have been specified have exemplary dimensions of instruments used in connection with the inventive procedure, it is to be appreciated that the gel viscosity, volume and disposition within the surgical annular track as well as the diameter of the track, width, depth and location are all parameters in the refractive change obtained in accordance with the invention.

What is claimed is:

1. A guiding device for facilitating the insertion of a delaminating device into an incision in the cornea for separating the lamellae of the cornea during a procedure for altering the radius of curvature of the cornea of an eye, said device comprising:

a first section consisting of a flat planar surface of uniform thickness for insertion into an incision in a cornea for guiding the end of a delaminating device between the lamellae of the cornea at a selected depth, and a second section, coupled to said guide section, for contacting the surface of the cornea to limit the depth of travel of said first section into the incision, wherein said first and second sections are coplanar, and wherein said first section extends curvillinearly from said second section.

2. The device as in claim 1, having a thickness of less than 300 microns.

3. The device as in claim 2, wherein its thickness measures between approximately 80 microns and approximately 100 microns.

4. The device as in claim 1, whereby said device is composed of stainless steel.

5. The device as in claim 1, having a rigidity greater than approximately $5 \times 10^6$ newtons/meter$^2$.

6. The device as in claim 1, whereby said device is composed of plastic.

7. The device as in claim 1, wherein said first and second sections are substantially perpendicular to each other.

8. The device as in claim 1, wherein the length of said first section ranges between 1 millimeter and 6 millimeters.

9. The device as in claim 1, whereby said second section contains portions for contacting the surface of cornea extending further than both outer edges of said first section.

10. A guide for facilitating the insertion of a curved delaminating device into an incision in the cornea for forming an annular channel between lamellae in the cornea at a desired depth spaced radially from the central region of the cornea during a procedure for altering the radius of curvature of the cornea of an eye, said guide comprising:

a first section consisting of a flat planar surface of uniform thickness for insertion into an incision in the cornea for guiding a curved delaminating device between lamellae at a desired depth within the incision; and a second section consisting of a flat planar surface of the same uniform thickness as said first section, coupled to and co-planar with said first section, for contacting the surface of the cornea to limit the depth of penetration of said first section into the incision in the cornea, wherein said first section extends curvillinearly from said second section at the same radius of curvature as the curved delaminating device.

11. The guide as in claim 10, having a uniform thickness of less than 300 microns.

12. The guide in claim 11, wherein its thickness measures between approximately 80 microns and 100 microns.

13. The guide as in claim 10, wherein the width of said first section is less than the thickness of the delaminating device.

14. The guide as in claim 10, having a rigidity greater than $5 \times 10^6$ newtons/meter$^2$.

15. The guide as in claim 10, wherein said device is composed of plastic.

\* \* \* \* \*